US012324926B2

(12) United States Patent
Brown et al.

(10) Patent No.: US 12,324,926 B2
(45) Date of Patent: Jun. 10, 2025

(54) DEVICE AND METHOD FOR ERADICATING PATHOGENS IN NASAL PASSAGES (71) Applicant: Neuraxis, Inc., Versailles, IN (US)

(72) Inventors: Christopher R. Brown, Greensburg, IN (US); Mark T. Volz, Batesville, IN (US)

(73) Assignee: Neuraxis, Inc., Versailles, IN (US)

(*) Notice: Subject to any disclaimer, the term of this patent is extended or adjusted under 35 U.S.C. 154(b) by 517 days.

(21) Appl. No.: 17/830,411

(22) Filed: Jun. 2, 2022

(65) Prior Publication Data

US 2022/0387817 A1 Dec. 8, 2022

Related U.S. Application Data (60) Provisional application No. 63/197,609, filed on Jun. 7, 2021.

(51) Int. Cl.
*A61N 5/06* (2006.01)

(52) U.S. Cl.
CPC ......... *A61N 5/0603* (2013.01); *A61N 5/0624* (2013.01); *A61N 2005/0607* (2013.01); *A61N 2005/0626* (2013.01); *A61N 2005/0632* (2013.01); *A61N 2005/0652* (2013.01); *A61N 2005/0663* (2013.01)

(58) Field of Classification Search
None
See application file for complete search history.

(56) References Cited

U.S. PATENT DOCUMENTS

| | | | |
|---|---|---|---|
| 4,305,402 | A | 12/1981 | Katims |
| 4,646,744 | A | 3/1987 | Capel |
| 4,865,048 | A | 9/1989 | Eckerson |

(Continued)

FOREIGN PATENT DOCUMENTS

| | | |
|---|---|---|
| AT | 395106 | 2/1992 |
| EP | 1335774 | 8/2003 |

(Continued)

OTHER PUBLICATIONS

International Search Report prepared for PCT/US2019/029172 mailed Jan. 28, 2020.

(Continued)

*Primary Examiner* — Carl H Layno
*Assistant Examiner* — Bryan McAllister Lee
(74) *Attorney, Agent, or Firm* — Barnes & Thornburg LLP (57) ABSTRACT

A device for eradicating at least one pathogen in a nasal passage of a human or animal may include a housing configured to be inserted into the nasal passage, at least one radiation source, configured to emit radiation, coupled to the housing such that at least a portion of a radiation emitting surface, upon insertion of the housing into the nasal passage, faces at least a portion of nasal lining of the nasal passage, and an electrical circuit carried by the housing and electrically connected to the at least one radiation source, the electrical circuit including at least one circuit component for controlling the at least one radiation source to emit the radiation to irradiate the nasal passage, the emitted radiation having a frequency or range of frequencies at which the at least one pathogen in the nasal passage, when irradiated by the emitted radiation, is eradicated.

20 Claims, 6 Drawing Sheets

(56) References Cited

U.S. PATENT DOCUMENTS

| | | |
|---|---|---|
| 5,084,007 A | 1/1992 | Malin |
| 5,094,242 A | 3/1992 | Gleason |
| 5,458,625 A | 10/1995 | Kendall |
| 6,296,652 B1 | 1/2001 | Qingmin |
| 6,212,433 B1 | 4/2001 | Behl |
| 7,092,849 B2 | 8/2006 | Lafitte |
| 7,103,417 B1 | 9/2006 | Segel |
| 8,308,784 B2 | 11/2012 | Streeter |
| 8,428,719 B2 | 4/2013 | Napadow |
| 8,465,531 B2 | 6/2013 | Aunio |
| 8,535,361 B2 | 9/2013 | Lim |
| 8,761,872 B2 | 6/2014 | Hinrichsen |
| 8,942,814 B2 | 1/2015 | Szeles |
| 9,662,269 B2 | 5/2017 | Brown |
| 9,782,584 B2 | 10/2017 | Cartledge |
| 9,839,577 B2 | 12/2017 | Brown |
| 9,901,734 B2 | 2/2018 | Bennett |
| 10,010,479 B2 | 3/2018 | Brown |
| 10,052,257 B2 | 8/2018 | Nageshwar |
| 10,058,478 B2 | 8/2018 | Schnetz |
| 10,086,199 B2 | 10/2018 | Robertson |
| 10,130,275 B2 | 11/2018 | Nageshwar |
| 10,130,809 B2 | 11/2018 | Cartledge |
| 10,413,719 B2 | 9/2019 | Brown |
| 10,471,276 B2 | 11/2019 | Beckner |
| 10,695,568 B1 | 6/2020 | Covalin |
| 10,806,928 B2 | 10/2020 | Sharma |
| 2003/0050470 A1 | 3/2003 | An |
| 2003/0149451 A1 | 8/2003 | Chomenky |
| 2004/0044390 A1 | 3/2004 | Szeles |
| 2006/0122675 A1 | 6/2006 | Libbus |
| 2007/0198063 A1 | 8/2007 | Hunter |
| 2008/0051852 A1 | 2/2008 | Dietrich |
| 2008/0071132 A1* | 3/2008 | Lamoureux ........... A61N 5/1015 600/7 |
| 2008/0249439 A1 | 10/2008 | Tracey |
| 2010/0004715 A1 | 1/2010 | Fahey |
| 2010/0113965 A1 | 5/2010 | Kanevsky |
| 2010/0168822 A1 | 7/2010 | Szeles |
| 2010/0262205 A1 | 10/2010 | De Ridder |
| 2011/0160811 A1 | 6/2011 | Walker |
| 2011/0190569 A1 | 8/2011 | Simon |
| 2012/0226333 A1 | 9/2012 | Szeles |
| 2012/0253427 A1 | 10/2012 | Aunio |
| 2013/0150923 A1 | 6/2013 | Schnetz |
| 2014/0081368 A1 | 3/2014 | Szeles |
| 2014/0370476 A1 | 12/2014 | Nageshwar |
| 2014/0371608 A1 | 12/2014 | Nageshwar |
| 2014/0371621 A1 | 12/2014 | Nageshwar |
| 2015/0112405 A1 | 4/2015 | Brown |
| 2015/0112411 A1 | 4/2015 | Beckman |
| 2015/0265830 A1 | 9/2015 | Simon |
| 2016/0074663 A1 | 3/2016 | De Ridder |
| 2016/0113526 A1 | 4/2016 | Nageshwar |
| 2016/0144175 A1 | 5/2016 | Simon |
| 2017/0143247 A1 | 5/2017 | Nageshwar |
| 2017/0197081 A1 | 7/2017 | Charlesworth |
| 2018/0064603 A1 | 3/2018 | Brown |
| 2018/0256917 A9* | 9/2018 | Lim ..................... A61N 5/0622 |
| 2018/0264282 A1* | 9/2018 | Bornstein ............ A61N 5/0624 |
| 2018/0280721 A1 | 10/2018 | Beckner |
| 2018/0296435 A1 | 10/2018 | Brown |
| 2019/0262229 A1 | 8/2019 | Brown |
| 2020/0121943 A1* | 4/2020 | Anderson ............ A61N 5/0603 |
| 2021/0128938 A1* | 5/2021 | Stasko ................... H01L 27/15 |

FOREIGN PATENT DOCUMENTS

| | | |
|---|---|---|
| EP | 2474339 | 11/2012 |
| WO | 2005001706 | 1/2005 |
| WO | 2011030210 | 3/2011 |
| WO | 2014200488 | 12/2014 |
| WO | 2014200489 | 12/2014 |
| WO | 2014200492 | 12/2014 |
| WO | 2014200498 | 12/2014 |
| WO | 2014207512 | 12/2014 |
| WO | 2015008154 | 1/2015 |
| WO | 2016151377 | 9/2016 |
| WO | 2019053625 | 3/2019 |

OTHER PUBLICATIONS

Extended Eurpean Search Report in Application No. 19850021.7-122 dated Dec. 8, 2021.

International Search Report prepared for PCT/US2020/039040 mailed Sep. 11, 2020.

Garcia-Argibay, M. et al., "Efficacy of binaural auditory beats in congnition, anxiety, and pain perception: a meta-analysis," Psychological Research, Aug. 2, 2018, vol. 83, pp. 357-372.

Palaniappan, R. et al., "On the binaural brain entrainment indicating lower heart rate variability," Cardiology, 2015, vol. 190, pp. 262-263.

Byung-Hyun, K. et al., "The Effect of White Noise and Pink Noise on the Brain Activity," The Journal of the Korea Contents Association, 2017, 17(5) pp. 491-498. (English machine-translation appended).

Da Silva, V.F. et al., "Stimulation by Light and Sound: Therapeutic Effects in Humans. Systematic Review," Clin Pract Epidemiol Ment Health, 2015, vol. 11, p. 150-4.

Gkolias, V. et al., "Reduced pain and analgesic use after acoustic binaural beats therapy in chronic pain—A double-blind randomized control cross-over trial," European J. Pain, 2020, 24(9) pp. 1716-1729.

Perez, H.D.O. et al., "Binaural Beats through the Auitory Pathway: From Brainstem to Connectivity Patterns," eNeuro, 2020, 7(2) 29 pages.

Mcconnel, P.A. et al., "Auditory driving of the autonomic nervous system: Listening to theta-frequency binaural beats post-exercise increases parasympathetic activation and sympathetic withdrawal," Frontiers in Psychology, 2014, vol. 5, 10 pages.

Graham, M.T. et al., "Simulations and human cadaver head studies to identify optimal acoustic receiver locations for minimally invasive photoacoustic-guided neurosurgery," Photoacoustics, 2020, 14 pages.

Grose, J.H. et al., "Binaural beat salience," Hear Res, 2013, 285(1-2) pp. 40-45.

Chaieb, L. et al., "Auditory beat stimulation and its effects on cognition and mood states," Frontiers in Psychiatry, 2015, vol. 6, pp. 1-9.

Ablen, V. et al., "Brainwave entrainment for better sleep and post-sleep state of young elite soccer players—study," European Journal of Sport Science, 2014, 14(5) pp. 393-402.

Wei, Q. et al., "Novel design of smart sleep-lighting system for improving the sleep environment of children," Technology and Health Care, 2019, vol. 27, pp. S3-S13.

Seshagiri, C.V. et al., "Response Properties of Neighboring Neurons in the Auditory Midbrain for Pure-Tone Stimulation: A Tetrode Study," J. Neurophysiol., 2007, vol. 98, pp. 2058-2073.

Padmanabhan, R. et al., "A prospective, randomised, controlled study examining binaural beat audio and pre-operative anxiety in patients undergoing general anaesthesia for day case surgery," Anasthesia, 2005, 60(9) pp. 874-877.

\* cited by examiner

DEVICE AND METHOD FOR ERADICATING PATHOGENS IN NASAL PASSAGES

CROSS-REFERENCE TO RELATED APPLICATION

This patent application claims the benefit of and priority to U.S. Provisional Patent Application Ser. No. 63/197,609, filed Jun. 7, 2021, the disclosure of which is incorporated herein by reference in its entirety.

TECHNICAL FIELD

The present disclosure relates generally to photobiomodulation devices, and more specifically to such devices configured to be inserted into at least one nasal passages of a human or animal for the purpose of eradicating one or more pathogens contained therein.

BACKGROUND

It is generally known that many pathogens can be eradicated by exposing such pathogens to radiation of a particular frequency or radiation in a particular range of frequencies. Pulsed Near-Infrared Photobiomodulation (PNIP) is another technique which uses radiant light energy to modify biological systems with a resulting therapeutic effect.

SUMMARY

The present disclosure may comprise one or more of the features recited in the attached claims, and/or one or more of the following features and combinations thereof. In a first aspect, a device for eradicating at least one pathogen in a nasal passage of a human or animal may comprise a housing configured to be inserted into the nasal passage, at least one radiation source, configured to emit radiation, coupled to the housing such that at least a portion of a radiation emitting surface of the at least one radiation source, upon insertion of the housing into the nasal passage, faces at least a portion of nasal lining of the nasal passage, and an electrical circuit carried by the housing and electrically connected to the at least one radiation source, the electrical circuit including at least one circuit component for controlling the at least one radiation source to emit the radiation to irradiate the nasal passage, the emitted radiation having a frequency or range of frequencies at which the at least one pathogen in the nasal passage, when irradiated by the emitted radiation, is eradicated.

A second aspect may include the features of the first aspect, and wherein the at least one radiation source is configured to emit radiation at a frequency in a range of visible red light or to produce radiation in a range of visible red light frequencies.

A third aspect may include the features of the first or the second aspect, and wherein the at least one radiation source may be configured to emit visible red light at a wavelength in a range of approximately 630 nm-900 nm.

A fourth aspect may include the features of any of the first through third aspects, and wherein the at least one radiation source comprises at least one light emitting diode (LED).

A fifth aspect may include the features of any of the first through fourth aspects, and may further comprise a source of electrical power carried by the housing, wherein the source of electrical power comprises at least one rechargeable or non-rechargeable battery.

A sixth aspect may include the features of any of the first through fifth aspects, wherein the at least one pathogen is at least one of on the nasal lining, on nasal hair or cilia extending from the nasal lining or trapped in mucous within the nasal passage, and wherein the emitted radiation has a frequency or range of frequencies configured to eradicate the at least one pathogen on the nasal lining, on the nasal hair or cilia extending from the nasal lining or trapped in the mucous within the nasal passage.

A seventh aspect may include the features of the any of the first through sixth aspects, and wherein the housing is elongated in an axial direction and has a curved outer periphery in a radial direction, and wherein the housing is configured to be moved axially along, and rotated within, the nasal passage to direct the emitted radiation to other portions of the nasal lining.

An eighth aspect may include the features of the seventh aspect, and wherein the at least one radiation source includes a plurality of radiation sources spaced apart axially along, and radially about, the housing.

A ninth aspect may include the features of any of the first through eighth aspects, and wherein the at least one pathogen includes COVID-19 virus.

In a tenth aspect, a nasal passage irradiation system may include the device having the features of any of the first through ninth aspects in which the electrical circuit includes wireless communication circuitry, and wherein the system may further comprise a mobile communication device including wireless communication circuitry configured to communicate wirelessly with the wireless communication circuitry of the device, the mobile communication device further comprising a processor programmed to control operation of the device by wirelessly communicating operating instructions thereto.

In an eleventh aspect, a nasal passage irradiation system may include the device having the features of any of the first through ninth aspects, and wherein the system may further comprise a mobile communication device hard-wire connectable to the device and including a processor programmed to control operation of the device by communicating, via a hard-wire connection between the device and the mobile communication device, operating instructions to the electrical circuit of the device.

In a twelfth aspect, a device for eradicating at least one pathogen in a nasal passage of a human or animal may comprise a housing, elongated in an axial direction and having a curved outer periphery in a radial direction, configured to be inserted into the nasal passage, at least one radiation source carried by the housing such that at least a portion of a radiation emitting surface of the at least one radiation source faces, with the housing inserted into the nasal passage, at least a portion of a nasal lining of the nasal passage, the at least one radiation source configured to emit radiation at a frequency or in a range of frequencies at which the at least one pathogen in the nasal passage, when irradiated by the emitted radiation, is eradicated, and an electrical circuit carried by the housing and electrically connected to the at least one irradiation source, the electrical circuit configured to control the at least one irradiation source to emit the radiation to irradiate the nasal passage, wherein the housing is configured to be moved axially along, and rotated within, the nasal passage to direct the emitted radiation along and about the nasal passage.

A thirteenth aspect may include the features of the twelfth aspect, and wherein the at least one pathogen is at least one of on the nasal lining, on nasal hair or cilia extending from the nasal lining or trapped in mucous within the nasal passage, and wherein the emitted radiation has a frequency or range of frequencies configured to eradicate the at least one pathogen on the nasal lining, on the nasal hair or cilia extending from the nasal lining or trapped in the mucous within the nasal passage.

A fourteenth aspect may include the features of the twelfth aspect or the thirteenth aspect, and wherein the at least one radiation source includes a plurality of radiation sources spaced apart axially along, and radially about, the housing.

A fifteenth aspect may include the features of any of the twelfth through fourteenth aspects, wherein the at least one pathogen includes COVID-19 virus.

In a sixteenth aspect, a nasal passage irradiation system may include the device having the features of any of the twelfth through fifteenth aspects in which the electrical circuit includes wireless communication circuitry, and wherein the system may further comprise a mobile communication device including wireless communication circuitry configured to communicate wirelessly with the wireless communication circuitry of the device, the mobile communication device further comprising a processor programmed to control operation of the device by wirelessly communicating operating instructions thereto.

In a seventeenth aspect, a nasal passage irradiation system may include the device having the features of any of the twelfth through fifteenth aspects and wherein the system may further comprise a mobile communication device hardwire connectable to the device and including a processor programmed to control operation of the device by communicating, via a hard-wire connection between the device and the mobile communication device, operating instructions to the electrical circuit of the device.

In an eighteenth aspect, a method is provided for eradicating at least one pathogen in a nasal passage of a human or animal with a device having an elongated housing and at least one radiation source coupled to the elongated housing such that radiation emitted by the at least one radiation source is directed outwardly away from the housing, the radiation being at a frequency or in a range of frequencies at which the at least one pathogen in the nasal passage, when irradiated by the emitted radiation, is eradicated. The method may comprise inserting the elongated a housing axially into the nasal passage, controlling, with electrical circuitry, the at least one radiation source to emit radiation toward a nasal lining of the nasal passage, and moving the housing at least one of axially along and rotatably within, the nasal passage to direct the emitted radiation at least one of correspondingly axially along and about the nasal passage.

A nineteenth aspect may include the features of the eighteenth aspect, wherein the electrical circuitry is carried by the housing and the device includes a switch or button operatively coupled to the housing, and wherein controlling the at least one radiation source may include manually actuating the switch or button to cause the electrical circuitry to control the at least one radiation source to emit the radiation.

A twentieth aspect may include the features of the eighteenth aspect, wherein at least some of the electrical circuitry is carried by a mobile communication device wirelessly or hard-wire connected to the device, and wherein controlling the at least one radiation source may comprise controlling by the mobile communication device, via a corresponding wireless or hard-wire connection to the device, the at least one radiation source to emit the radiation.

DESCRIPTION OF THE ILLUSTRATIVE EMBODIMENTS

For the purposes of promoting an understanding of the principles of this disclosure, reference will now be made to a number of illustrative embodiments shown in the attached drawings and specific language will be used to describe the same.

This disclosure relates to devices and techniques for irradiating at least a portion of one or more nasal passages of a human or animal for the purpose of eradicating one or more pathogens contained therein. For purposes of this disclosure, the term "pathogen" and variants thereof shall be understood in to mean any microorganism which is able to enter a human or animal via at least one nasal passage, e.g., through physical contact or by breathed air, and to then cause or produce an infection or disease in the human or animal. Examples of such pathogens, and variants thereof, which may be eradicated in human or animal nasal passages using the device(s) and techniques described herein may include, but are not limited to, any virus, without limitation, that is capable of replicating or multiplying within living cells of the human or animal, examples of which may include, but are not limited to, Coronaviruses (including, but not limited to, Covid 19), Influenza viruses, Rhinoviruses, Varicella viruses, Measles virus, Mumps virus, Hantavirus, and the like, any bacteria without limitation, any fungus without limitation, and any parasite without limitation. Also for purposes of this disclosure, the terms "eradicate," "eradicating" and variants thereof, as this term relates to one or more pathogen, shall be understood to mean to kill or destroy one or more pathogens and/or to render inoperable one or more pathogens in a human and/or animal. Further still, for purposes of this disclosure, the term "nasal passage" shall be understood to include the nasal lining of a nostril, nasal hair/cillia along the nasal lining and at least a portion of one or more nasal or sinus cavities in fluid communication with the nostril.

Figure 1:
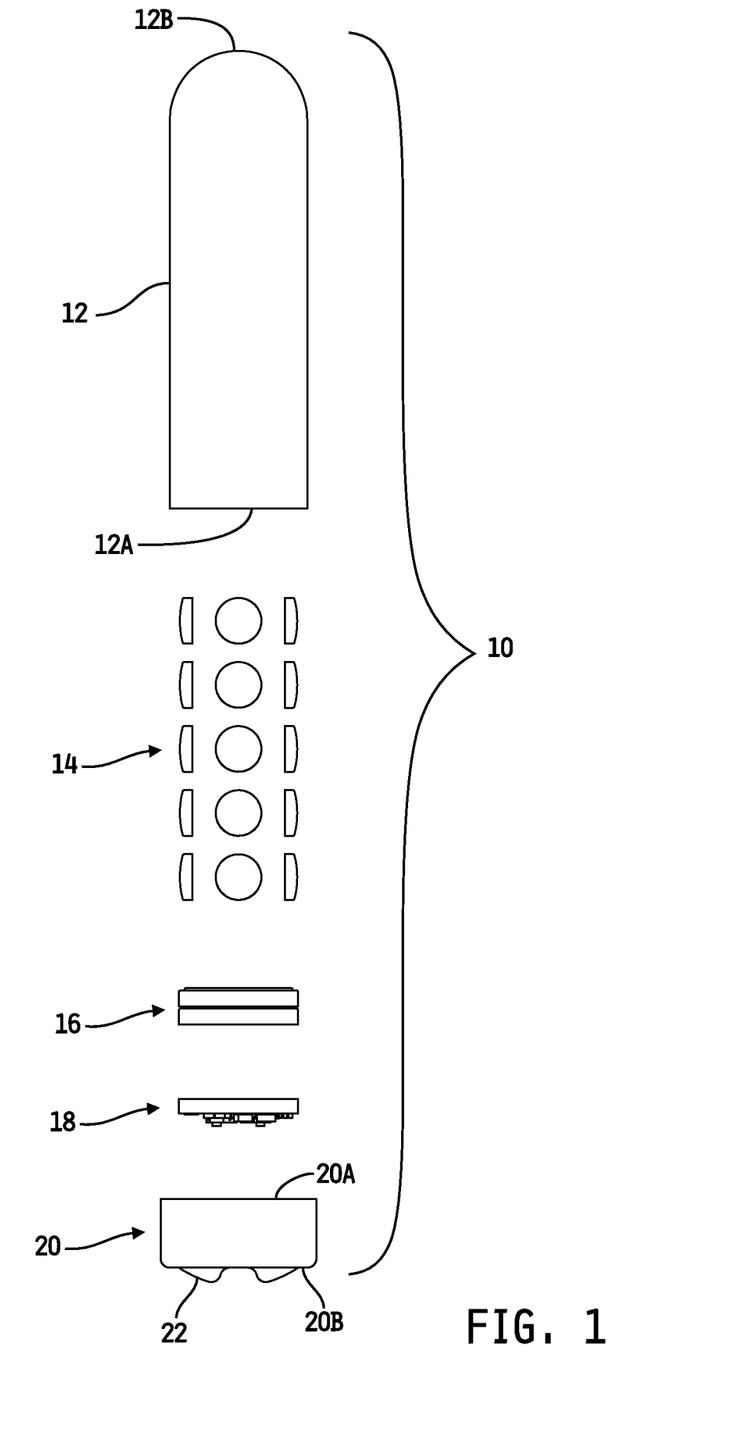
FIG. 1 is an exploded view of an embodiment of a device for eradicating one or more pathogens in one or more nasal passages.
Figure 2:
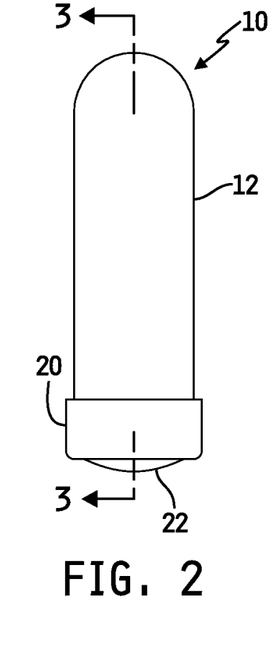
FIG. 2 is an assembled view of the device illustrated in FIG. 1.
Figure 3:
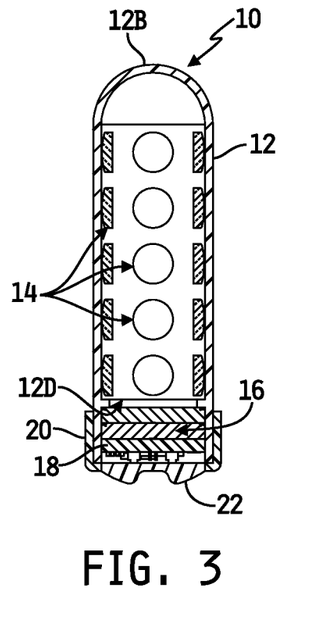
FIG. 3 is a cross-sectional view of the device of FIG. 2, as viewed along section lines 3-3 of FIG. 2.

Referring to FIGS. 1-3, an embodiment is shown of a device 10 configured to be inserted into a nasal passage of a human or animal, and to be controlled to irradiate the epithelium/mucosal lining ("nasal lining") of the nasal passage for the purpose of eradicating at least one pathogen on the nasal lining and/or trapped in mucous and/or nasal hair/cillia along the nasal lining. It will be appreciated that the device 10 may be used to irradiate the nasal lining of only a single nasal passage, or may alternative be used to irradiate the nasal linings of both nasal passages, one after the other. In the illustrated embodiment, the device 10 includes an housing 12 configured to receive a number of radiation sources 14 therein, a source 16 of electrical power, electrical circuitry 18 for controlling operation of the radiation sources 14 and an endcap 20 configured to be coupled to the housing 12. The housing 12 is illustratively elongated in the axial direction and has a curved outer periphery in the radial direction, although it will be understood that other shapes of the housing 12 are contemplated by this disclosure.

Figure 4:
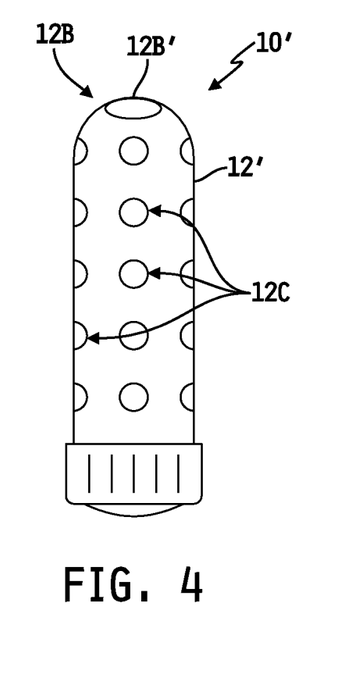
FIG. 4 is an assembled view of an alternate embodiment of a device for eradicating one or more pathogens in one or more nasal passages.

The elongated housing 12 has an open end 12A that is configured to receive the components 14, 16, 18 therein, and a dome-shaped closed end 12B opposite the open end 12A. In the illustrated embodiment, the housing 12 is made of a light transmissive material, and the radiation sources 14 are arranged along the interior surface of the housing 12 such that the radiation sources 14 are spaced apart from one another longitudinally and radially, and such that the radiation sources 14 together radially span the interior surface of the housing 12. In some embodiments, one or more of the radiation sources 14 is/are affixed or otherwise mounted to the interior surface of the housing 12. In one alternate embodiment of the device 10', illustrated by example in FIG. 4, the housing 12' may define a number of passageways 12C therethrough each sized to receive a portion of a corresponding radiation source 14 therethrough. In the alternate embodiment illustrated in FIG. 4, the housing 12' may be formed of any suitable plastic or other material which may be light transmissive, opaque or non-light transmissive.

In one example embodiment, the housing 12, 12' is approximately 60 mm in length and approximately 17 mm in diameter. In the embodiment illustrated in FIGS. 1-3, 20 radiation sources 14 are each approximately 2 mm in diameter and spaced apart approximately 10 mm from one another in the longitudinal and radial directions. In the embodiment illustrated in FIG. 4, 20 passageways 12C are spaced apart approximately 10 mm from one another in the longitudinal and radial directions, and are each sized to receive therein a respective radiation source 14 approximately 2 mm in diameter, and an additional passageway 12B' is defined through the closed end 12B of the housing 12' and is sized to receive therein an additional radiation source 14 approximately 2 mm in diameter. In the alternate embodiment illustrated in FIG. 4, the radiation sources 14 are mounted to the housing 12' via the passageways 12C. It will be understood that the foregoing dimensions, number of radiation sources and spacing therebetween are provided only by way of example, and that in alternate embodiments one or more of the foregoing dimensions may be larger or smaller and/or the device 10, 10' may include more or fewer radiation sources 14 and/or the one or more radiation sources 14 may be distributed differently along and/or about the housing 12, 12', e.g., one or more linear arrangements of the radiation sources 14 longitudinally along at least a portion of the housing 12, 12', one or more radial arrangements of the radiation sources at least partially about the housing 12, 12', etc.

Figure 6:
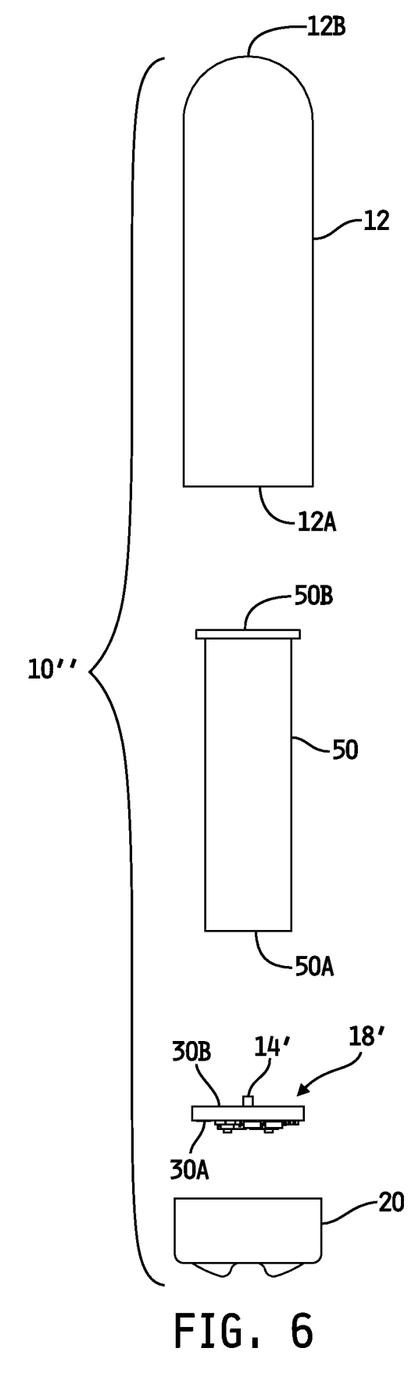
FIG. 6 is an exploded view of yet another embodiment of a device for eradicating one or more pathogens in one or more nasal passages.

As illustrated by example in FIG. 6, another alternate embodiment of the device 10'' includes a conventional light pipe 50 sized to be received within the housing 12 and configured to transmit, transfer or otherwise pass radiation therethrough. In some embodiments, the light pipe 50 may be formed of a transparent or translucent material, and in other embodiments the light pipe 50 may be formed of an opaque material configured to transmit, transfer or otherwise pass at least some radiation therethrough. In this alternate embodiment, one open end 50B of the light pipe 50 is received within the housing 12 adjacent to or near the closed end 12B, and an opposite open end 50A of the light pipe 50 is configured to be coupled to or otherwise extend over an alternate embodiment of the electrical circuitry 18' which includes at least one radiation source 14' mounted thereto so as to direct radiation into the light pipe 50 via the open end 50A thereof. In some embodiments, the at least one radiation source 14' may include only a single radiation source, and in alternate embodiments the at least one radiation source 14' may include two or more radiation sources 14'. In any case, the housing 12 is, in this embodiment, formed of at least a partially light-transmissive, e.g., transparent, translucent or opaque, material configured to pass therethrough radiation exiting the light pipe 50.

In one embodiment of any of the devices 10, 10', 10''', the one or more radiation sources 14, 14' are each light emitting diodes (LEDs) or LED arrays. In alternate embodiments, the one or more radiation sources 14, 14' may be provided in the form of one or any combination of one or more other conventional radiation sources configured to produce radiation at any single frequency or in any range of frequencies. It will be understood that whereas the embodiment illustrated in FIGS. 1-3 includes 20 radiation sources 14 equally-spaced apart radially about and longitudinally along the housing 12, the embodiment illustrated in FIG. 4 includes these as well as an additional radiation source 14 positioned centrally through the closed end 12B of the housing 12', and the embodiment illustrated by example in FIGS. 6-7 include a single radiation source 14', alternate embodiments may include more or fewer such radiation sources equally or non-equally spaced apart radially or otherwise positioned relative to the housing 12.

In one example embodiment, the one or more radiation sources 14, 14' are each configured to produce radiation at a frequency, or in the frequency range, of red visible light so as to eradicate pathogens in the nasal passage(s). In one particular embodiment, the one or more radiation sources 14, 14' are each illustratively configured to produce radiation at 930 nm. It will be understood, however, that one or more of the radiation sources 14, 14' may alternatively be configured to produce radiation at any frequency in the frequency range of red visible light, or alternatively still be configured to produce radiation at any frequency or in any range of frequencies, visible or otherwise, which will result in eradication of one or more pathogens in the nasal passage when irradiated thereby.

As best illustrated in FIG. 3, a stop 12D is positioned between the radiation sources 14 and the source 16 of electrical power so as to prevent the components 16, 18 from entering the portion of the housing 12, 12' in which the radiation sources 14 are positioned. In one embodiment, the stop 12D is integral with the housing 12, 12', although in other embodiments the stop 12D may be a component separate from the housing 12, 12'.

In the illustrated embodiment, the source 16 of electrical power includes two so-called "coin" or "button-cell" batteries. In one embodiment, each battery is configured to produce approximately 3 volts, and the two batteries are electrically connected in series to provide a total of 6 volts. In alternate embodiments, at least one of the batteries may be configured to produce a greater or lesser voltage. In any case, it will be understood that whereas the embodiment illustrated in FIGS. 1-3 includes two series-connected batteries, alternate embodiments may include more or fewer such batteries. In other alternate embodiments in which the device 10, 10', 10" is hard-wire connected to an electronic device, e.g., as illustrated by example in FIG. 10, electrical power may be provided to the device 10, 10', 10" by the electronic device and the source 16 of electrical power may, in such embodiments, be omitted.

Figure 10:
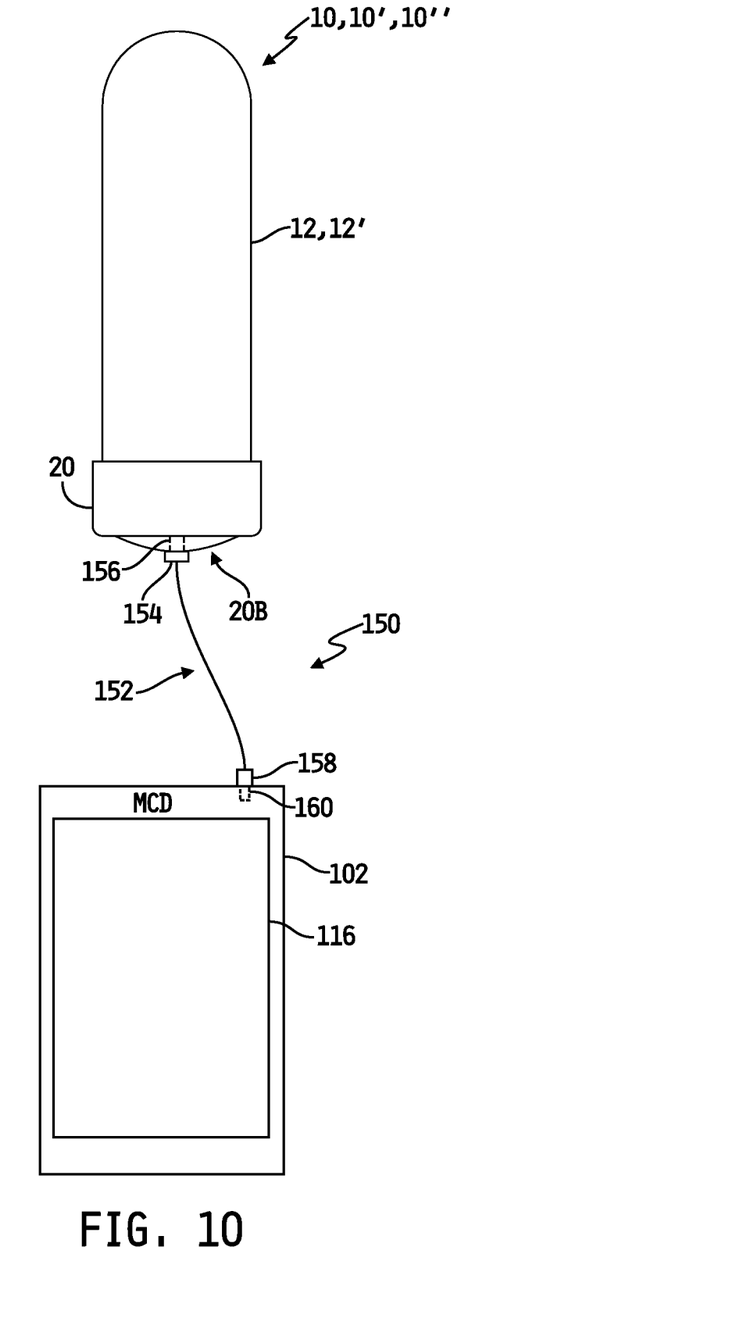
FIG. 10 is a simplified diagram of an embodiment of a pathogen eradication system illustrating any of the devices of FIGS. 1-7 connected via a wired connection to a mobile communication device, wherein the device is controlled by a software application executed by the mobile communication device.

As illustrated by example in FIGS. 1-4 and 6, the electrical circuit or circuitry 18, 18' is received within and mounted to the housing 12, 12' and/or to the endcap 20, and an open end 20A of the endcap 20 is then mounted to the open end 12A of the housing 12, 12' such that the housing 12, 12' carries the source 16 of electrical power and the electrical circuit 18, 18'. Opposite the open end 20A, the endcap 20 has a closed end 20B. In some embodiments, the closed end 20B may include one or more push-type and/or screw-type buttons 22 for turning on/off the device 10, 10', 10" and/or for controlling operation, e.g., switching rate and/or duty cycle, of the radiation source(s) 14, 14'. In some alternate embodiments, the closed end 20B of the endcap 20 may alternatively or additionally include an electrical connector configured to be electrically connected to a remote electronic device, one example of which is illustrated in FIG. 10.

Figure 5:
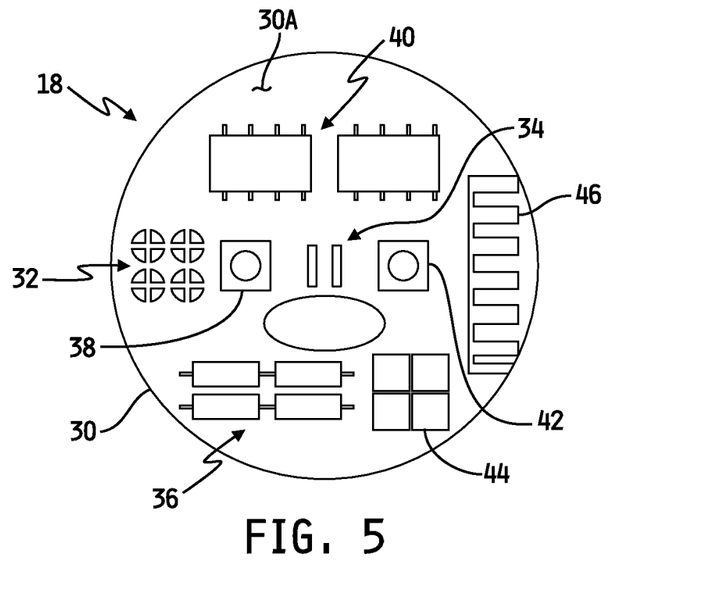
FIG. 5 is a top plan view of an embodiment of the control circuitry of the devices illustrated in FIGS. 1-4.

Referring now to FIG. 5, an embodiment of the electrical circuit or circuitry 18, suitable for implementation in either or both of the devices 10, 10, is shown. In the illustrated embodiment, the electrical circuit 18 includes a circuit board 30 having a number of different circuit components mounted to one surface 30A thereof so as to face toward the open end 12A of the housing 12, 12' (and away from the closed end 12B). In alternate embodiments, one or more (or all) of the circuit components may be mounted to the opposite surface 30B of the circuit board 30. In any case, the circuit board 30 may illustratively be a conventional rigid, semi-flexible or flexible circuit board configured for surface-mounting and/or through-hole mounting of circuit components thereto. For example, the circuit board 30 illustratively includes electrical terminals or pads 32 configured for connection of electrical power leads or wires thereto, e.g., example, positive (+) and negative (or ground) (−) terminals of the source 30 of electrical power may be connected to suitable wires which extend into electrical connection with the terminals or pads 32. The circuit board 30 further includes radiation source electrical terminals 34 or pads configured for conventional connection of leads or wires extending from the one or more radiation sources 14.

Figure 7:
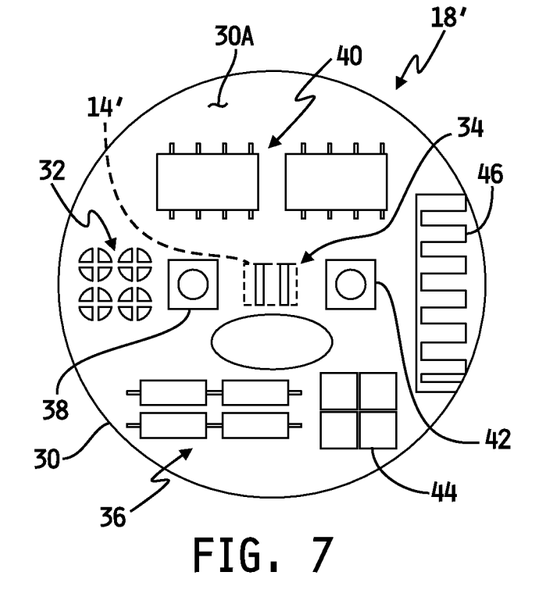
FIG. 7 is a top plan view of an embodiment of the control circuitry of the device illustrated in FIG. 6.

In an alternate embodiment of the electrical circuit or circuitry 18' illustrated by example in FIG. 7, the one or more radiation sources 14' is/are mounted to an opposite surface 30B and electrically connected to the terminals 34 in a conventional manner such that radiation produced by the one or more radiation sources 14' is directed into the light pipe 50. The electrical circuit or circuitry 18' may otherwise be identical to the electrical circuit or circuitry 18.

Referring now to both FIGS. 5 and 7, four resistors 36 are mounted to the circuit board 30, and each is electrically coupled at one end through a normally-off switch 38 to the electrical power terminals 32, and each is electrically connected at an opposite end through the terminals or pads 32 to a different respective group of the radiation sources 14 or, in the case of the electrical circuit 18', to the radiation source(s) 14'. In some alternate embodiments, more or fewer resistors 36 may be mounted to the circuit board 30 and electrically connected between the electrical power terminals 32 and one or more of the one or more radiation sources 14, 14', one resistor for each radiation source 14, 14'. In applications in which the embodiment 10" of FIG. 6 is implemented, for example, a single resistor 36 may suffice.

The electrical circuit 18, 18' further illustratively includes a number of integrated circuits 40 mounted to the circuit board 30. In some embodiments, at least one of the integrated circuits 40 is electrically connected to the switch 38 and is configured to control the switch 38 between on and off states at a constant or predefined or programmable switching rate. In some embodiments, the switch 38 may act as a mode switch to control the one or more radiation sources 14, 14' between different on/off times. In one example embodiment, which should not be considered to be limiting in any way, the switching rate may range between 0+−40 Hz, wherein 0+ should be understood to mean any switching rate greater than 0 but less than 1 Hz, although other switching rates, or varying switching rates, may alternatively be used. In other embodiments, the switching rate may be zero such that the one or more radiation sources 14, 14' is/are constantly on when the switch is in the on state.

In some embodiments in which the switching rate is greater than 0, the duty cycle of the switching rate is approximately 50%, although in other embodiments the duty cycle may be greater or less than 50%. In some embodiments, one or more of the integrated circuits 40 may including at least one processor circuit, e.g., microprocessor or microcontroller, to control the switching rate and/or duty cycle, and in other embodiments other conventional switching circuitry may be implemented. In some embodiments, at least one of the integrated circuits 40 is a conventional driver circuit operatively coupled to the source 16 of electrical power, the switch 38 and/or the resistor(s) 36, and is operable to supply electrical power, and in some embodiments regulate voltage and/or current, from the source 16 of electrical power to the one or more radiation sources 14, 14'.

The electrical circuit 18 further illustratively includes an on/off switch 42 mounted to the circuit board 30. In some embodiments in which the device 10 is self-controlled, the one or more buttons 22 may be operatively coupled to the switch 42, and the device 10, 10' may be powered on and off and/or controlled via manual actuation of one of the one or more buttons 22. In other embodiments, the device 10, 10' may be wirelessly connected to a remotely located mobile (or stationary) electronic control device (MCD), e.g., as illustrated by example in FIG. 8, and in such embodiments the device 10, 10' may be powered on and off and/or be controlled by the MCD. In some such embodiments, the one or more buttons 22 may include only device on/off capability, and in other such embodiments the one or more buttons 22 may be omitted. In still other embodiments, the device 10, 10 may be hard-wire connected to the MCD, e.g., as illustrated by example in FIG. 10, and in such embodiments such embodiments the device 10, 10' may be powered on and off and/or be controlled by the MCD. In some such embodiments, the one or more buttons 22 may include only device on/off capability, and in other such embodiments the one or more buttons 22 may be omitted. Examples of the remotely located mobile (or stationary) control device (MCD) may include, but are not limited to, a laptop, tablet or personal computer, a mobile communication device such as a mobile phone, smart watch or the like, or other mobile or stationary electronic control device or system.

In some embodiments in which the end cap 20 includes one or more buttons 22 and in which the device 10, 10', 10" is configured to turn the one or more radiation sources 14, 14' on and off at one or more frequencies and/or with one or more duty cycles, the button(s) 22 may include a single button or multiple buttons. In one example embodiment, the end cap 20 may include multiple buttons; one for turning on and off the device 10, 10', 10" and one or more for selecting the switching frequency and/or duty cycle. In another example embodiment, the end cap 20 may include only a single button 22 which may be used to select a desired switching frequency and/or duty cycle, as well as to activate and deactivate the device 10, 10', 10". As one specific example of this embodiment, which should not be considered limiting in any way, each press or push of the single button 22 may have the following results or effects; push 1=10 Hz switching rate of the one or more radiation sources 14, 14', push 2=20 Hz switching rate of the one or more radiation sources 14, 14', push 3-30 Hz switching rate of the one or more radiation sources 14, 14' and push 4=off. It will be understood that in this example, the device 10, 10', 10" could be modified to include more or fewer switching rates. In embodiments which are configured to operate at only a single switching rate, or to operate only in a constant-on or off mode, only a single button 22 may be implemented, or the button 22 may be omitted and a screw-on end cap 20 may be used to turn on and off the device 10, 10', 10". In any of the foregoing embodiments, the button(s) 22 may alternatively be omitted and all control of the radiation source(s) 14, 14', e.g., on/off and/or switching frequency and/or duty cycle, may be controlled by an MCD.

In embodiments in which the device 10, 10', 10" is configured to be wirelessly controlled by a wirelessly-connected control device, wireless communication circuitry may be mounted to the circuit board 30 and electrically connected to at least the switch 42. In the embodiments illustrated in FIGS. 5 and 7, for example, a wireless communication control circuit 44 is shown by example as being mounted to the circuit board 30 and electrically connected to the switch 42 (either directly or via one or more of the integrated circuits 40), and a wireless communication antenna 46 is also mounted to the circuit board 30 and electrically connected to the wireless communication circuit 44. In one such embodiment, the wireless communication circuit 44 is illustratively implemented in the form of a conventional Bluetooth® controller, and the antenna 46 is a conventional Bluetooth® antenna array, and the Bluetooth® controller 44 is operable in a conventional manner to receive and, in some embodiments, to transmit information in accordance with a conventional Bluetooth® communication protocol. It will be understood, however, that Bluetooth® represents only one example wireless communication protocol that may be implemented in the device 10, 10', 10", and that in alternate embodiments the wireless communication control circuit 96 and antenna 46 may be configured for wireless communication in accordance with one or more other conventional wireless communication protocols. In embodiments in which the device 10, 10', 10" is configured to be manually controlled, e.g., via one or more switches 22, the circuit 44 and the antenna 46 may be omitted from the circuitry board 30. In some embodiments of the device 10, 10', 10", an audible device may also be mounted to the circuit board 30 for the purpose of providing an audible indication of one or more aspects of operation of the device 10, 10', 10", e.g., such as on/off, operating frequency, time of use, etc. In some such embodiments, the audible device may be provided in the form of one or more buzzers, beepers, etc., one or more speakers for conveying one or more audible sounds, etc.

In embodiments in which the electrical circuit 30 includes wireless communication circuitry as just described, a mobile communication device (MCD) is illustratively provided and programmed to control operation of the device 10, 10', 10" via instructions communicated wirelessly thereto. Such a programmed MCD may also or alternatively be used to control operation of the device 10, 10', 10" in embodiments in which the device 10, 10', 10" is hard-wire connected to the MCD.

Figure 8:
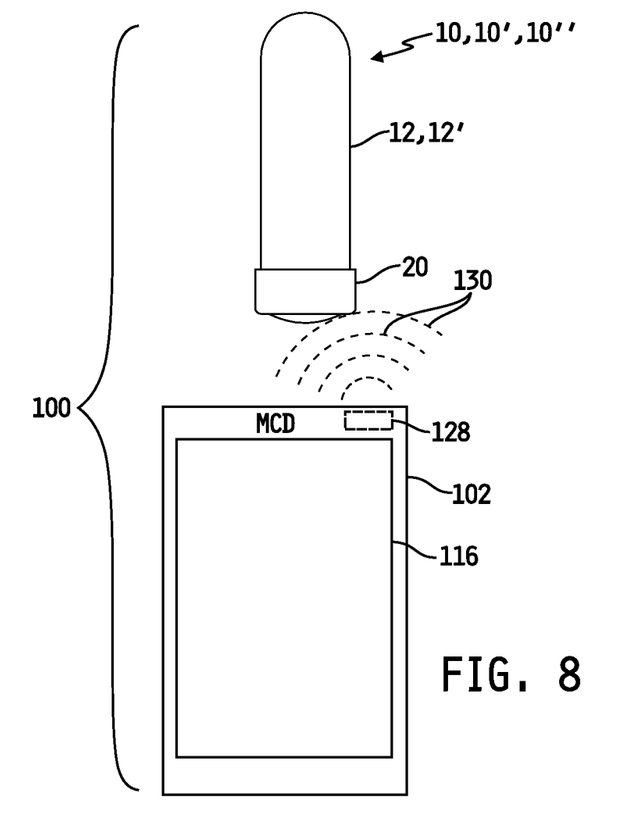
FIG. 8 is a simplified diagram of an embodiment of a pathogen eradication system illustrating any of the devices of FIGS. 1-7 controlled wirelessly by a software application executed by a mobile communication device.

Referring now to FIG. 8, an embodiment is shown of a wirelessly controlled nasal passage irradiation system 100 in which a mobile communication device (MCD) 102 with wireless communication capability is configured, i.e., programmed, to control operation of at least one device 10, 10', 10" for eradicating at least one pathogen in at least one nasal passage of a human or animal. As illustrated by example in FIGS. 11A and 11B, the tubular housing 12, 12' of the device 10, 10', 10" is inserted into a nasal passage 204 of a nose 202 of a human 200 (or animal) with the closed, e.g., domed, end 12B, 12B' extending first and furthest into the nasal passage 204. The MCD 102 is operable to communicate wirelessly with the electrical circuit 18 carried by the device 10, 10', 10" as depicted graphically in FIG. 8 by the wireless communication arcs 130, and is therefore operable to wirelessly control operation of the device 10', 10', 10". In some embodiments of the device 10, 10', 10", the device 10', 10', 10" may, after insertion into the nasal passage, be rotated about a central longitudinal axis defined through the nasal passage 204 so as to cause radiation produced by the one or more radiation sources 14, 14' to irradiate as much of the nasal lining as possible. Alternatively, the device 10, 10', 10" may not be so rotated after insertion. The depth of penetration of the housing 12, 12' into the nasal passage 204 may vary between individuals, and it is expected that any particular user will insert the device 10, 10', 10" into the nasal passage 204 as far as will be comfortable and/or as deemed adequate or necessary by that user.

In one embodiment, the MCD 102 may be a conventional mobile cell phone, e.g., a so-called smart phone, although in alternate embodiments the MCD 102 may be provided in the form of other conventional or application-specific wireless communication devices. Example of such devices include, but are not limited to, a conventional personal data assistant (PDA), a tablet computer, a key fob, a smart watch, e.g., a stand-alone device or communicatively coupled to a mobile cell phone, a conventional wireless remote control device, or the like. It will be understood that although the device 10, 10', 10" is illustrated in FIG. 8 as being controlled, at least in part, by the MCD 102, in other embodiments which do not include the MCD 102 the device 10, 10', 10" may be controlled manually as described above.

Figure 9:
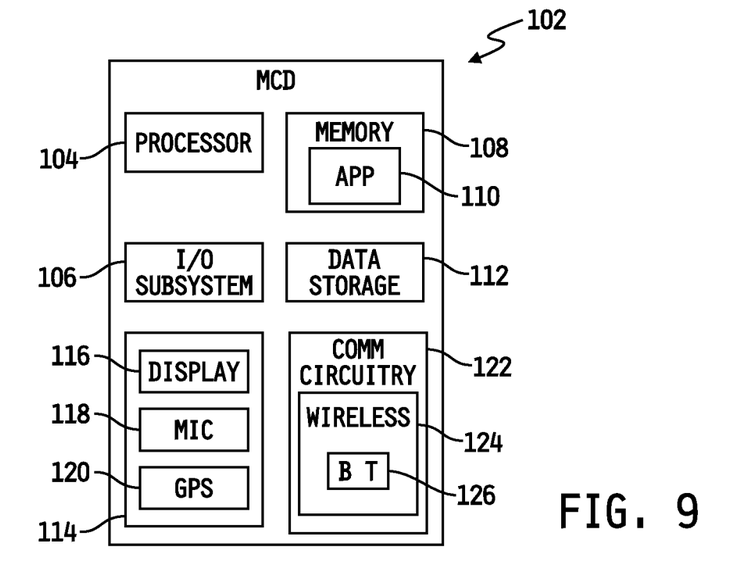
FIG. 9 is a simplified schematic block diagram of the mobile communication device of FIG. 8.

Referring now to FIG. 9, an embodiment of the MCD 102 is shown which illustratively includes a conventional processor 104 operatively coupled to an I/O subsystem 106 which is, in turn, coupled to a memory 108, a data storage 112, a number of peripheral devices 114 and communication circuitry 122. The memory 108 illustratively has stored therein an executable application 110 in the form of instructions executable by the processor 104 to control operation of the device 10, 10', 10" in any manner as described herein. The data storage 112 is illustratively implemented in the form of one or more conventional memory devices in which data relating to the user of the MCD 102 and/or data relating to operation of the device 10, 10', 10" is stored.

The peripheral devices 114 may include any conventional peripheral devices typically included on a mobile communication device 102 of the type just described. Examples include, but are not limited to, a conventional display screen 116 as also illustrated in FIG. 8, e.g., touch-controlled or otherwise, a conventional microphone 118 and a conventional GPS module (e.g., including a conventional GPS receiver and associated antenna). Those skilled in the art will recognize other conventional devices that may be included in the peripheral devices 114, and it will be understood that any such other conventional devices are intended to be included within the scope of this disclosure.

The communication circuitry 122 illustratively includes wireless communication circuitry 124, and the wireless communication circuitry 124 may illustratively include any number of wireless communication modules each configured to carry out wireless communications according to a particular communications protocol. Examples include, but are not limited to, Wi-Fi/internet communications, cellular communications, near-field communications, and the like. In the embodiment illustrated in FIG. 9, the wireless communication circuitry 124 alternatively or further includes a Bluetooth® module 126, e.g., in the form of a conventional Bluetooth® controller, that is electrically connected to a conventional Bluetooth® antenna 128 as illustrated by example in FIG. 8. As such, the MCD 102 is configured to conduct wireless communications with the device 10, 10', 10" according to a conventional Bluetooth® communications protocol. In some embodiments, such wireless communications may be one-way; such that the MCD 102 may only wirelessly transmit information to the device 10, 10', 10" and the device 10, 10', 10" may only receive information wirelessly transmitted by the MCD 102, or vice versa, and in other embodiments such wireless communications may be two-way; such that the MCD 102 and the device 510, 10', 10" may both wirelessly transmit information to, and receive information wirelessly transmitted by, the other.

In some embodiments in which the device 10, 10', 10" includes wireless (or wired) communication capability as described above, the processor 104 of the MCD 102 is operable to control operation of the device 10', 10', 10", in whole or in part, by executing the application 110 stored in the memory 108. In one embodiment, for example, at least one of the integrated circuits 40 mounted to the circuit board 30 of the device 10, 10', 10" is a conventional timer circuit coupled to the switch 38, and the application 110 illustratively includes instructions which, when executed by the processor 104, cause the processor 104 to control the wireless communication circuitry 126, 128 to wirelessly transmit one or more signals to the device 10, 10', 10" which carry(s) instructions to activate the timer circuit to cause the timer circuit to turn on and off the switch 38 at a predetermined pulse rate, at a selected pulse rate, at a pulse rate that is swept over a range of pulse frequencies, or to cause the timer circuit to turn on the switch 38 for a predetermined duration or until manually turned off. The Bluetooth® controller 44 on-board the device 10, 10', 10" is, in turn, operable to receive such instructions and to control the timer circuit to operate as just described. In other embodiments in which the pulse rate of the timer circuit is programmable, the application 110 illustratively includes instructions which, when executed by the processor 104, cause the processor 104 to control the wireless communication circuitry 126, 128 to wirelessly transmit one or more signals to the device 10, 10', 10" which carry(s) instructions to activate the timer circuit to cause the timer circuit to turn on and off the switch 38 at a selected pulse rate. In some embodiments, the duty cycle of the timer circuit may be static, e.g., 50%, and in other embodiments the duty cycle may be programmable and selectable as just described with respect to the pulse rate.

In other embodiments, at least one of the integrated circuits 40 mounted to the circuit board 30 of the device 10, 10', 10" may be a conventional processor coupled to, or including, a memory and to the switch 38, and such a memory may include instructions executable by the processor of the device 10, 10', 10" to cause the processor to control operation of the switch 38. In some such embodiments, the pulse rate and/or duty cycle of the radiation source(s) 14, 14' may be static and in other embodiments may be selectable as described above.

In any case, the application 110 illustratively presents a user interface on the display screen 116 via which the user may selectively, i.e., via manual interaction with a touch-selectable interface displayed on the screen 116 and/or via manual selection of a button, switch or key of the MCD 102, control at least part of the operation of the device 10, 10', 10" including, for example, use duration, e.g., 15-minute use intervals. In some embodiments, the application 110 may also provide for automatic capture of use data, e.g., calendar date, time of day, duration of use, location of use (e.g., via GPS data), etc., user entry of personal data, e.g., name, age, user activity level during use, user physiological and/or psychological state, e.g., hot, cold, calm, nervous, anxious, etc., and/or diagnostic data relating to operation of the device 10, 10', 10" (e.g., in embodiments in which the device 10, 10', 10" is configured to wirelessly transmit such data to the MCD 102).

Referring now to FIG. 10, another embodiment is shown of a nasal passage irradiation system 150 in which the mobile communication device (MCD) 102 is hard-wire connected, via an electrical cable 152, to a device 10, 10', 10" for eradicating at least one pathogen in at least one nasal passage of a human or animal. In the illustrated embodiment, an electrical connector 156 is defined in, or mounted to, the end cap 20 of the device 10, 10', 10", and is configured to electrically connect to a complementarily configured electrical connector 154 defined at, or mounted to, one end of the electrical cable 152. Another electrical connector 160 is defined in, or mounted to, the MCD 102, and is configured to electrically connect to a complementarily configured electrical connector 158 defined at, or mounted to, the opposite end of the electrical cable 152. In some embodiments, the MCD 102 is programmed, e.g., as described above, to control, in whole or in part, operation of the device 10, 10', 10".

Figure 11A:
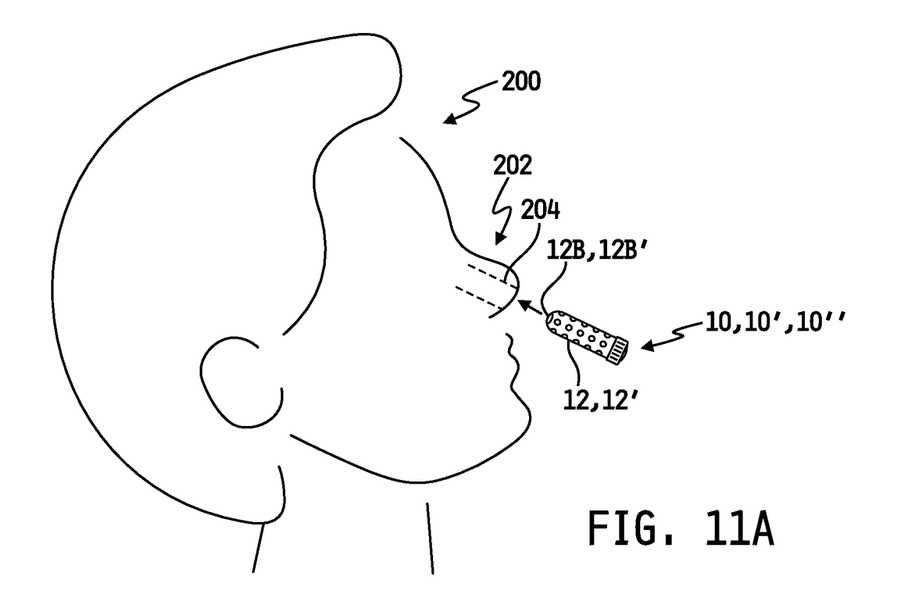
FIG. 11A is a simplified diagram of any of the devices of FIGS. 1-7 shown aligned with a nasal passage of a human.
Figure 11B:
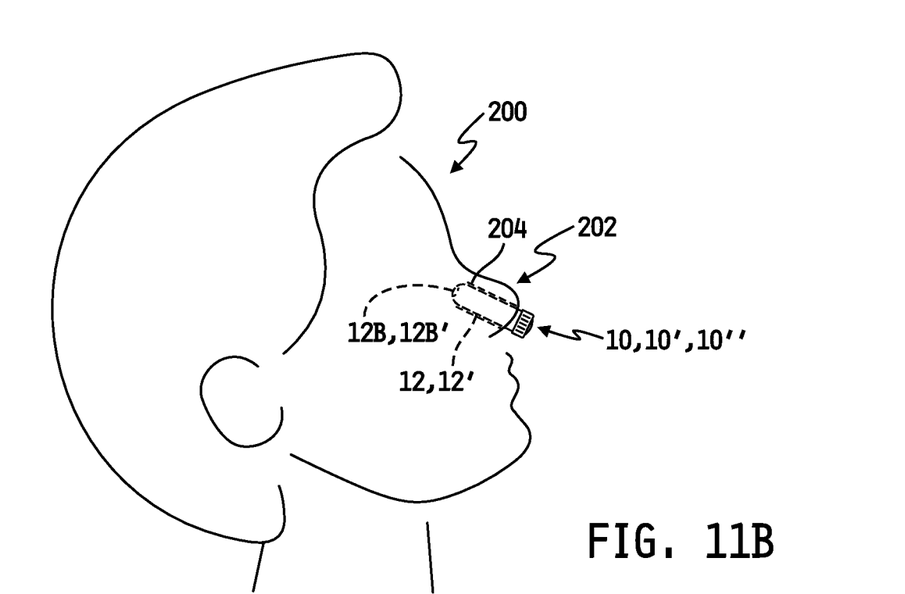
FIG. 11B is a simplified diagram similar to FIG. 11A and showing the device inserted in one of the nasal passages of the human.

As depicted by example in FIGS. 11A and 11B, the device 10, 10', 10" is insertable into a nasal passage 204 of a nose 202 of a human 200 (or animal), and is controllable, e.g., manually and/or via an MCD 102, to irradiate the nasal passage 204 to eradicate one or more pathogens contained thereon and/or therein, as described above. Alternatively or additionally, the device 10, 10', 10" may be controlled, e.g., manually and/or via an MCD 102, in a photobiomodulation mode to irradiate the nasal lining with pulsed radiation so as to stimulate at least one nerve bundle and/or at least one arterial branch under in the nasal lining. In either case, the housing 12, 12' of the device 10, 10', 10" is illustratively configured to be moved axially along, and rotated within, the nasal passage 204 to direct the emitted radiation along and about the nasal passage 204. In this regard, and in one example method of operating the device 10, 10', 10", which should not be considered limiting in any way, the housing 12, 12' of the device 10, 10', 10" may be first inserted axially into a nasal passage 204 of the nose 202, and then axially and/or rotably moved, along and/or about the nasal passage 204 to direct the radiation emitted by the radiation sources 14, 14' along and/or about the nasal passage 204 to eradicate one or more pathogens in the nasal passage 204. Both nasal passages can be treated sequentially, and either or both may be repeatedly treated at any time with any desired frequency.

A potential entry route of a pathogen into a human or animal is directly through branches of the cranial nerves found in the epithelium and supportive tissues of the external nares (nose) and the sinus cavities. The olfactory nerve serves as a potential rapid trans-neural avenue to spread the virus into the central nervous system. The sino/nasal tract is considered a major route of, for example, SARS-Covid-2 transmission into the respiratory tract both as an initial and secondary site of host infection. Virus shedding also contributes as a systemic in-host transmission mechanism. Viral shedding refers to the expulsion and release of virus following successful reproduction during a host-cell infection. Once replication of the virus has been completed and the initial host cells are exhausted the virus exits the initial host site resulting in the virus trans-locating to other body regions. In the case of SARS-Covid 19, for example, the secondary site is often the lungs. Transmission of the virus initiates a cytokine cascade resulting in an intense inflammatory process which occurs in the lung tissue resulting in potential lung damage, hypoxia, and death.

Research has indicated that photobiomodulation therapy (PBMT), in the form of light in the red spectrum (e.g., 630 nm-900 nm) is capable of preventing the loss of heme-function oxygen transport (Hb02) resulting in an increase of oxygen rate consumption by mitochondria, increasing ATP production, reducing the inflammatory cascade and reducing the lethality of COVID-19. PBMT is known to affect the cranial arteries, nerves, cranial perfusion pressure, and modulate neural oscillations, and is believed to be a useful therapeutic tool when delivered intra-nasally.

Pulsed, rather than steady or static radiation, is believed to reduce the potential overheating of the adjacent nasal tissues. Chromophores contain both heme and copper centers which absorb light in the infra-red and near infra-red regions. It is hypothesized that photons disassociate inhibitory nitric oxide leading to an increase in electron transport, mitochondrial membrane potential, ATP production and concurrently activate light-sensitive ion channels allowing calcium to enter the cell after initial photon absorption activates signaling pathways. This acts as a vasodilator and increases lymphatic flow. While vasodilation reverses shortly after the light stimulation is removed, the changes following exposure to light are known to last for days, weeks, or even months. The long-lasting effects cannot be explained simply by the activation of the mitochondria or stimulation of blood flow alone and is postulated to be as a result of activation of signaling pathways and transcription factors that change protein expression.

The mechanisms of action of PBMT illustratively include:
(1) activating the interferons which have antiviral activity, thereby increasing T lymphocytes, helps regulate immune system reactions and stimulates lymphocytes and macrophages,
(2) activating phagocytes to engulf and remove microorganisms,
(3) increasing micro and macro-circulation to increase tissue resistance to the pathogen and its affects, and
(4) increasing oxygen saturation of tissues which in turn increases cell metabolism and regeneration of tissues.

Anti-inflammatory and regenerative effects of PBM have been observed in the treatment of such diverse conditions as allergic lung inflammation, vocal cord injuries, periodontitis, and oral lesions. It is postulated that irradiation at various points along the respiratory system, including the nares and sinus area may be helpful in the management of COVID-19 pneumonia by reducing the nasal/sinus viral load reducing the viral population and reducing viral shedding. It is further postulated that PBMT in the nasal passage to irradiate arterial branches and branches of cranial nerves beneath the epithelium/mucosal lining of the nose may be helpful in reducing local inflammation, functionally altering the neurovascular tissues which would include any branches of the cranial nerves, and/or hastening restoration of the sense of smell and/or the sense of taste in humans following infection by the COVID-19 virus. Other benefits and/or uses of the nasal lining irradiation device 10, 10', 10" illustrated by example in the attached drawings and described herein will occur to those skilled in the art, and it will be understood that any and all such benefits and/or uses are intended to fall within the scope of this disclosure.

While this disclosure has been illustrated and described in detail in the foregoing drawings and description, the same is to be considered as illustrative and not restrictive in character, it being understood that only illustrative embodiments thereof have been shown and described and that all changes and modifications that come within the spirit of this disclosure are desired to be protected.

What is claimed is:

1. A device for eradicating at least one pathogen in a nasal passage of a human or animal, the device comprising:
    a housing configured to be inserted into the nasal passage,
    at least one radiation source, configured to emit radiation, coupled to the housing such that at least a portion of a radiation emitting surface of the at least one radiation source, upon insertion of the housing into the nasal passage, faces at least a portion of nasal lining of the nasal passage, and
    an electrical circuit carried by the housing and electrically connected to the at least one radiation source, the electrical circuit including at least one circuit component for controlling the at least one radiation source to emit the radiation to irradiate the nasal passage, the emitted radiation having a frequency or range of frequencies at which the at least one pathogen in the nasal passage, when irradiated by the emitted radiation, is eradicated.

2. The device of claim 1, wherein the at least one radiation source is configured to emit radiation at a frequency in a range of visible red light or to produce radiation in a range of visible red light frequencies.

3. The device of claim 1, wherein the at least one radiation source is configured to emit visible red light at a wavelength in a range of approximately 630 nm-900 nm.

4. The device of claim 1, wherein the at least one radiation source comprises at least one light emitting diode (LED).

5. The device of claim 1, further comprising a source of electrical power carried by the housing, wherein the source of electrical power comprises at least one rechargeable or non-rechargeable battery.

6. The device of claim 1, wherein the at least one pathogen is at least one of on the nasal lining, on nasal hair or cilia extending from the nasal lining or trapped in mucous within the nasal passage,
and wherein the emitted radiation has a frequency or range of frequencies configured to eradicate the at least one pathogen on the nasal lining, on the nasal hair or cilia extending from the nasal lining or trapped in the mucous within the nasal passage.

7. The device of claim 1, wherein the housing is elongated in an axial direction and has a curved outer periphery in a radial direction,
and wherein the housing is configured to be moved axially along, and rotated within, the nasal passage to direct the emitted radiation to other portions of the nasal lining.

8. The device of claim 7, wherein the at least one radiation source includes a plurality of radiation sources spaced apart axially along, and radially about, the housing.

9. The device of claim 1, wherein the at least one pathogen includes COVID-19 virus.

10. A nasal passage irradiation system, comprising:
the device of claim 1, wherein the electrical circuit includes wireless communication circuitry, and
a mobile communication device including wireless communication circuitry configured to communicate wirelessly with the wireless communication circuitry of the device, the mobile communication device further comprising a processor programmed to control operation of the device by wirelessly communicating operating instructions thereto.

11. A nasal passage irradiation system, comprising:
the device of claim 1, and
a mobile communication device hard-wire connectable to the device and including a processor programmed to control operation of the device by communicating, via a hard-wire connection between the device and the mobile communication device, operating instructions to the electrical circuit of the device.

12. A device for eradicating at least one pathogen in a nasal passage of a human or animal, the device comprising:
a housing, elongated in an axial direction and having a curved outer periphery in a radial direction, configured to be inserted into the nasal passage,
at least one radiation source carried by the housing such that at least a portion of a radiation emitting surface of the at least one radiation source faces, with the housing inserted into the nasal passage, at least a portion of a nasal lining of the nasal passage, the at least one radiation source configured to emit radiation at a frequency or in a range of frequencies at which the at least one pathogen in the nasal passage, when irradiated by the emitted radiation, is eradicated, and
an electrical circuit carried by the housing and electrically connected to the at least one radiation source, the electrical circuit configured to control the at least one radiation source to emit the radiation to irradiate the nasal passage,
wherein the housing is configured to be moved axially along, and rotated within, the nasal passage to direct the emitted radiation along and about the nasal passage.

13. The device of claim 12, wherein the at least one pathogen is at least one of on the nasal lining, on nasal hair or cilia extending from the nasal lining or trapped in mucous within the nasal passage,
and wherein the emitted radiation has a frequency or range of frequencies configured to eradicate the at least one pathogen on the nasal lining, on the nasal hair or cilia extending from the nasal lining or trapped in the mucous within the nasal passage.

14. The device of claim 12, wherein the at least one radiation source includes a plurality of radiation sources spaced apart axially along, and radially about, the housing.

15. The device of claim 12, wherein the at least one pathogen includes COVID-19 virus.

16. A nasal passage irradiation system, comprising:
the device of claim 12, wherein the electrical circuit includes wireless communication circuitry, and
a mobile communication device including wireless communication circuitry configured to communicate wirelessly with the wireless communication circuitry of the device, the mobile communication device further comprising a processor programmed to control operation of the device by wirelessly communicating operating instructions thereto.

17. A nasal passage irradiation system, comprising:
the device of claim 12, and
a mobile communication device hard-wire connectable to the device and including a processor programmed to control operation of the device by communicating, via a hard-wire connection between the device and the mobile communication device, operating instructions to the electrical circuit of the device.

18. A method for eradicating at least one pathogen in a nasal passage of a human or animal with a device having an elongated housing and at least one radiation source coupled to the elongated housing such that radiation emitted by the at least one radiation source is directed outwardly away from the housing, the radiation being at a frequency or in a range of frequencies at which the at least one pathogen in the nasal passage, when irradiated by the emitted radiation, is eradicated, the method comprising:
inserting the elongated housing axially into the nasal passage,
controlling, with electrical circuitry, the at least one radiation source to emit radiation toward a nasal lining of the nasal passage, and
moving the elongated housing axially along and rotatably within, the nasal passage to direct the emitted radiation axially along and about the nasal passage.

19. The method of claim 18, wherein the electrical circuitry is carried by the elongated housing and the device includes a switch or button operatively coupled to the elongated housing,
and wherein controlling the at least one radiation source includes manually actuating the switch or button to cause the electrical circuitry to control the at least one radiation source to emit the radiation.

20. The method of claim 18, wherein at least some of the electrical circuitry is carried by a mobile communication device wirelessly or hard-wire connected to the device,
and wherein controlling the at least one radiation source comprises controlling by the mobile communication device, via a corresponding wireless or hard-wire connection to the device, the at least one radiation source to emit the radiation.

* * * * *